United States Patent [19]

Moore

[11] Plant 4,512

[45] Mar. 18, 1980

[54] MINIATURE ROSE PLANT

[76] Inventor: Ralph S. Moore, 2519 E. Noble Ave., Visalia, Calif. 93277

[21] Appl. No.: 969,449

[22] Filed: Dec. 14, 1978

[51] Int. Cl.[2] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant characterized by the deep red color of buds and flowers and further identified by the unique "moss" on the buds.

1 Drawing Figure

1

The present invention relates to a new and distinct variety of hardy, dwarf, bush type rose plant of the miniature class; the variety being primarily characterized—as to novelty —by deep red buds and flowers which in general color effect are similar to Honest Abe, miniature (plant patent pending).

The variety is further characterized by:

Lightly mossed buds, said moss being soft to the touch.

An abundance of bloom, with flowers borne singly or several to the stem in loose clusters.

Little or no fragrance.

A plant which is vigorous, of rounded somewhat spreading shape with semi-glossy small foliage with pointed leaflets; the buds and flowers being similar in form and size to June Time (miniature—U.S. Plant Pat. No. 2,563).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observatiion, as a cross between Fairy Moss (miniature—U.S. Plant Pat. No. 3,082) as the seed parent, and Fire Princess (miniature—U.S. Plant Pat. No. 3,084), as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Toy Balloon.

2

Flowers borne: Singly and several together (3 to 5) on slender, wirey, quite thorny stems.

Quantity of bloom: Abundant both outside and in greenhouse.

Bud:

*Peduncle.*—Medium length; slender but sturdy; erect; medium to light green; hairs — numerous (very small) hairs and thorns.

*Before calyx breaks.*—Size — small. Form long; pointed with numerous soft hairs and moss-like appendages on surface of bud; with foliaceous parts extending beyond the tip of the bud equal to one-half or more of its length. Color — medium green.

*As calyx breaks.*—Color — dark red — near Chrysanthemum Crimson 824 (or darker). Opening: opens well in all weather.

Bloom:

*Size when fully open.*—Small, averaging about 35 mm ($1\frac{3}{8}$").

*Petalage.*—Double to very double — averaging about 45 or more petals, arranged regularly plus occasional petaloids.

*Form.*—Flat to high centered at first, becoming more rounded with petals rolled loosely outward, and later at maturity full with petals remaining in similar shape and position. Open flowers; usually have no stamens.

Petals: Fairly thick; satiny to velvety on inside and satiny on outside surface.

*Shape.*—Outside petals, broad lanceolate (nearly round) with very short acute tip; intermediate — broad lanceolate with short acute tip; inside — lanceolate with acute or rounded tip.

Color: Newly opened flower from a plant grown in plastic greenhouse Nov. 20, 1978.

*Outside petal.*—Outside surface — near Chrysanthemum Crimson 824/2 with small near white area at base. Inside surface — near Chrysanthemum Crimson 824/1 or 824/2 with darker red overlay and small near white area at base.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — color dark velvety red. Three days open — color similar to newly opened flowers. Behavior — opens well in all weather. Spent petals may persist for short time then drop off. Flower longevity (May 1978) — plant in pot 5–8 days. Cut flowers at living room temperature 6 days.

Reproductive organs:

*Stamens.*—Few or none.

*Filaments.*—Quite short, near white.

*Anthers.*—Few, usually none.

*Pollen.*—Little or none.

*Pistils.*—Average number.

*Styles.*—Rather uneven; varying length; bunched; color — near white.

*Stigmas.*—Near white.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes 3 or 7) leaflets; small; leathery; semi-glossy.

*Leaflets.*—Shape: broad lanceolate; nearly oval; apex acute; base rounded. Margin serrate.

*Color.*—Medium green; new growth — normal (medium) green, sometimes reddish.

*Rachis.*—Medium strength; upper side may have numerous tiny short hairs; grooved; underside moderately thorny with several short hairs and tiny prickles.

*Stipules.*—Fairly short; narrow to medium width; short length narrow points which turn out at both more and less than 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Many; slender; may be straight or hooked slightly downward; color; brown. Prickles — numerous; hairs — few or none.

*Branches.*—Color: medium green. Thorns: numerous; medium length; slender; nearly straight, may be inclined slightly downward. Medium to short oval base. Prickles: numerous. Hairs: usually none.

*Young shoots.*—Color: medium green. Thorns; quite numerous, slender; usually straight, (sometimes inclined slightly downward); color — greenish or pinkish.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers which are (1) dark red, similar to Honest Abe (miniature—plant patent pending) in color, the buds and flowers resembling June Time (miniature—U.S. Plant Pat. No. 2,563) in size and shape and (2) the bud (sepals) being lightly covered with short moss, said moss being soft to the touch and further characterized by a plant which is vigorous and compact, easy to propagate from softwood cuttings or by budding, with an abundance of flowers borne singly or several to the stem in loose clusters.

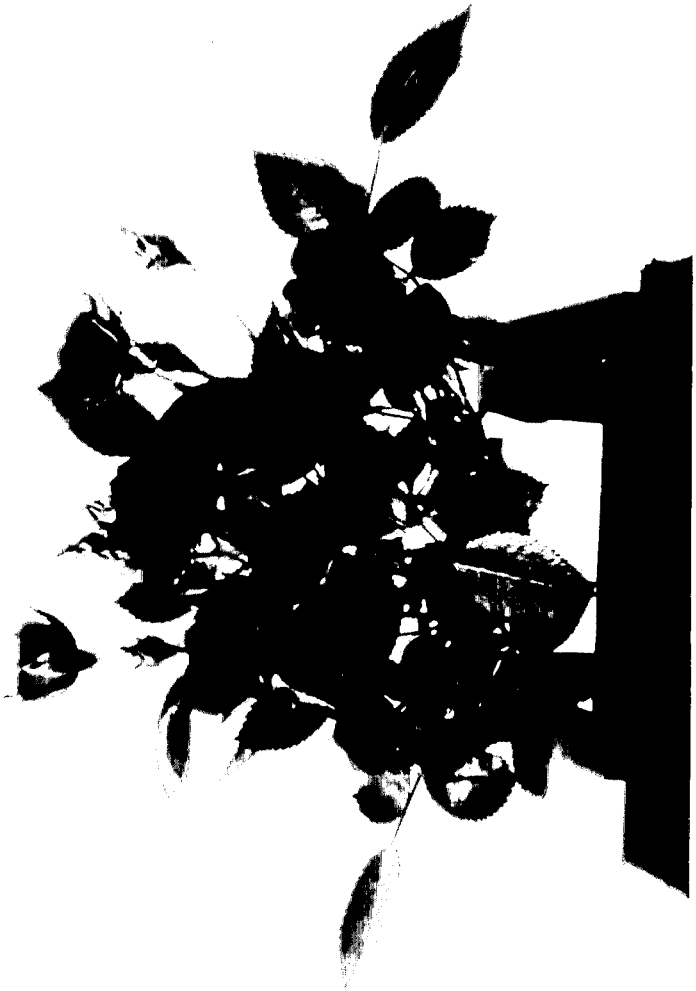

* * * * *